United States Patent
Moran et al.

(10) Patent No.: US 9,339,838 B2
(45) Date of Patent: May 17, 2016

(54) AEROSOL GENERATOR ASSEMBLY

(75) Inventors: Declan Moran, Claregalway (IE); Gavan O'Sullivan, Gort (IE)

(73) Assignee: NORTEV LIMITED, Claregalway, Galway (IE)

( * ) Notice: Subject to any disclaimer, the term of this patent is extended or adjusted under 35 U.S.C. 154(b) by 413 days.

(21) Appl. No.: 13/697,517

(22) PCT Filed: May 10, 2011

(86) PCT No.: PCT/EP2011/057547
§ 371 (c)(1),
(2), (4) Date: Jan. 29, 2013

(87) PCT Pub. No.: WO2011/141475
PCT Pub. Date: Nov. 17, 2011

(65) Prior Publication Data
US 2013/0119151 A1 May 16, 2013

(30) Foreign Application Priority Data
May 13, 2010 (EP) .................................. 10162791

(51) Int. Cl.
A61M 15/00 (2006.01)
A61M 11/00 (2006.01)
B05B 17/06 (2006.01)
B05B 17/04 (2006.01)
B05B 17/00 (2006.01)
A61M 15/02 (2006.01)

(52) U.S. Cl.
CPC .......... *B05B 17/0676* (2013.01); *A61M 11/005* (2013.01); *A61M 15/0085* (2013.01); *A61M 15/025* (2014.02); *A61M 2202/0468* (2013.01); *B05B 17/0646* (2013.01)

(58) Field of Classification Search
CPC .... B05B 17/06; B05B 17/04; B05B 17/0615; B05B 17/0646; B05B 12/081; B05B 17/0669; A61M 15/0085; A61M 15/0018; A61M 15/00; A61M 11/00; A61M 15/0065; A61M 15/008; A61M 11/005; A61M 16/10

USPC ............ 128/200.11–200.24, 203.12, 203.15; 239/102.2, 338

See application file for complete search history.

(56) References Cited

U.S. PATENT DOCUMENTS

| | | | | |
|---|---|---|---|---|
| 7,472,701 | B2 * | 1/2009 | Pfichner et al. | 128/203.12 |
| 2005/0011514 | A1 * | 1/2005 | Power et al. | 128/200.14 |
| 2005/0034719 | A1 * | 2/2005 | Feiner et al. | 128/200.21 |
| 2006/0102172 | A1 * | 5/2006 | Feiner et al. | 128/200.14 |
| 2008/0308096 | A1 * | 12/2008 | Borgschulte et al. | 128/200.14 |

FOREIGN PATENT DOCUMENTS

| | | |
|---|---|---|
| WO | 93/10910 A1 | 6/1993 |
| WO | 2006/125677 A1 | 11/2006 |
| WO | 2009/042187 A1 | 4/2009 |
| WO | 2011/033092 A1 | 3/2011 |

* cited by examiner

*Primary Examiner* — Annette Dixon
(74) *Attorney, Agent, or Firm* — Knobbe Martens Olson & Bear LLP

(57) ABSTRACT

An aerosol generator assembly comprising a vibratable piezo ceramic body (2) having first and second opposing sides, an aperture (o) defined in the vibratable body and extending through the body from the first side to the second side and having a layer of electrical contact material on each side of the vibratable body, the vibratable body being vibratable by application of an electrical signal thereto; a vibratable member (1) with pores defined therein, the vibratable member mounted across the aperture; and an electrical contact material free-zone (4) is provided on at least one side of the body about the aperture, characterized in that the electrical contact material free-zone and the vibratable member are dimensioned so that the vibratable member is mountable directly onto the vibratable body on top thereof within the electrical contact material free-zone such that a gap area free of electrode contact material is formed between the terminating edge of the electrical contact material and the periphery of the vibratable member.

13 Claims, 4 Drawing Sheets

AEROSOL GENERATOR ASSEMBLY

CROSS-REFERENCE TO RELATED APPLICATIONS

This application is the U.S. National Phase under 35U.S.C. §371 of International Application PCT/EP2011/057547, filed May 10, 2011, which claims priority to European Patent Application 10162791.7, filed May 13, 2010.

FIELD OF THE INVENTION

The invention relates to aerosol generators and in particular to liquid aerosol droplet generators which are often electronically controlled for example those of the piezo-based type. More particularly, the invention relates to improvements to electronic piezo-based liquid aerosol generator assemblies.

BACKGROUND TO THE INVENTION

There have existed for some time piezo-based aerosol generators for use in the generation of aerosolized liquids, for example, in the construction of nebulisers for aerosolization of pharmaceutical solutions for therapeutic use by delivery through aerosol inhalation to the lungs.

Existing electronic piezo based aerosol generator devices typically comprise an actuator unit which generally utilises a support substrate (generally a disc-shaped metal, such as stainless steel or a brazing metal or alloy) having a central orifice adapted to accommodate a nozzle plate, which typically has a dome shaped central portion surrounded by an edge which is suitable for mounting the plate onto the support substrate. The nozzle plate is provided with a plurality of orifices of about 3-5 microns in diameter. A ring of actuatable material, typically a piezoelectric ("piezo") ceramic material, is mounted onto the support substrate about the central orifice. Generally, the nozzle plate is in the form of a vibratable member and typically comprises a thin flexible membrane material surrounded by a mounting flange or edge. International Publication No. WO 2009/042187 describes a typical example of such a device. Radial oscillations or vibrations generated within the piezoceramic material are transferred through the support substrate to the flexible membrane and induce vertical vibration/flexing of the nozzle plate. It is the vertical vibrating and/or flexing action of the membrane of the nozzle plate which aerosolizes a liquid by driving the liquid through the apertures in the nozzle plate by way of the vertical flexing action. A dome shaped nozzle plate amplifies the effect of the vibration. The vertical vibration/flexing of the nozzle plate membrane produces a micropumping action at the surface of nozzle plate in contact with liquid to force liquid through the plurality of orifices in the nozzle plate membrane, thereby generating an aerosolized fluid, which typically takes the form of, for example, liquid droplets, such as those of a dissolved drug, suspended in air.

In addition to holding the piezo ceramic disc and the nozzle plate, the support substrate amplifies and transmits the oscillations/vibrations generated in the piezo ceramic to the flexible membrane nozzle plate. The orifices in the nozzle plate may be funnel shaped to maximise pumping efficiency and aerosol formation. The support also acts as a base structure to isolate the piezo ceramic body from the liquid path by providing a foundation for sealant materials such as epoxy and silicone, which are typically used to isolate the piezo ceramic body from liquid and aerosol. Although the use of a support substrate has associated advantages, one drawback is that use of such substrate requires additional manufacturing processing steps and requires use of special process steps such as brazing and use of special materials such as conductive adhesives and a sealant is typically required to prevent shorting. All of these steps add to manufacturing costs and complexity. Corrosion between the support substrate and nozzle plate and/or piezo ceramic body can be another problem which can occur where moisture ingress and can lead to premature failure of the actuator.

Prior art piezo ceramic materials suitable for actuators typically comprise the piezo ceramic material which is coated with a layer of electrical contact material, typically in the form of a (thin) layer or film of a conductive material which is deposited or coated on top of the ceramic surface, in the form of a metallized electrode. For example, a film of silver electrode can be coated on the surface area of at least one face of the piezo surface. Generally, this film of electrical contact material is provided on at least one of the entire opposing surfaces of the piezo carried out during manufacture, for example, by a screen printing or sputtering process. The film of conductive material making up the electrical contact material is generally in the order of 3 to 10 micron thickness. It typically covers at least one entire side of the piezo material. The film is needed to facilitate passage of current across/through the piezo material over all or a large proportion of its surface area to cause it to vibrate. In other words, the film conductive material making up the electrical contact material functions as an electrode to assist in power transfer through the body of the piezo ceramic material. A number of prior art devices utilise distinct regions or areas of screen printed conductive material making up the electrical contact material electrodes on the ceramic body to form a drive electrode and a sense electrode which monitors and ensures resonant vibration of the body is maintained. Where present, the support substrate (typically a metal support ring) may act as an electrode for the (opposite face of the) piezo ceramic body, thereby providing a completed circuit which facilitates application of an electrical signal to be applied across the piezo for inducing vibration thereof. Generally, the piezo will be bonded to the support substrate in a manner that does not hinder electrical conduction, for example, brazing or through use of a conducting adhesive. If the metal supporting substrate is to act as an electrode, it is necessary to have the supporting substrate conductively attached (for example, bonded by a conductive epoxy material) to the piezo to ensure current can flow from the electrode through the piezo. The entire actuator can then be coated with sealant materials to resist moisture ingress. Such sealants can however result in undesirable dampening of vibration or may lead to inconsistent actuation from device to device.

Three factors affecting the lifetime of piezo ceramic actuators are humidity, operating voltage and temperature. In particular, the piezo ceramic materials used in piezo ceramic actuator are moisture sensitive. Ingressing moisture and the electric field applied can cause electrochemical transport processes in the piezo ceramic actuator, which are accelerated by higher temperatures. While it is straightforward to develop a waterproof piezo ceramic actuator utilising waterproof coatings, making them vapour tight is more difficult. When exposed to moisture over time, the piezo ceramic actuator frequently short circuits. For example a short circuit can occur between the electrodes or screen printed surface films of conducting material, which can cause irreparable damage to the piezo ceramic actuator and leads to premature device failure. To minimise this problem, prior art piezo ceramic actuator devices are often coated in a sealant material (for example, an epoxy coating) that is cured to protect the piezo ceramic actuator circuit from moisture. The entire circuit may then be encased in a protective silicon layer to increase insulation. However, water vapour can still penetrate these polymers and so the piezo ceramic actuator generally needs to be sealed from moisture ingress. Sealing increases the manufacturing costs of the piezo ceramic actuator unit. Furthermore, the attachment area where the nozzle plate is attached to the supporting substrate is particularly susceptible to corrosion and thus leaking, making the device more prone to shorting.

Overall, the prior art designs are complex and several processing steps are required to produce the device making manufacture more costly. The corrosion issues and tendency towards circuit shorting are significant problems and limit the lifetime of the device. Furthermore, since in arrangements utilising piezo materials mounted onto supporting substrates, the piezo is bonded to the support substrate, the natural vibration of the piezo device may be dampened. The resulting dampening of the actuation of the piezo ceramic actuator thus reduces the efficiency of the device, and requires supply of higher power to compensate, risking premature failure through burn out and increasing risk of moisture induced shorting.

In piezo ceramic-based aerosol generators, flow rate is controlled by voltage applied across the piezo ceramic body. For smaller piezo ceramic actuator devices, the maximum operating voltage may be limited by the piezo ceramic actuators dimensions. The optimum operating voltage must be selected carefully to achieve optimum performance requirements as too high a voltage may damage the device. Devices therefore that give higher flow rates using lower operating voltages are desirable as the lifetime of the device will be extended when compared to piezos ceramic actuators requiring higher operating voltages to achieve the same flow rate. Therefore, dampening should be avoided as far as possible.

Thus, both the construction and the energy usage of existing piezo ceramic actuator devices could be improved upon.

U.S. Pat. No. 5,823,428 and International Publication No. WO 93/10910 each describes an apparatus for atomizing a liquid in which the liquid is passed through tapered perforations in a vibrating membrane. In the embodiments described, the perforate vibrating member and a piezoelectrical annulus are bonded onto an apertured support substrate which is an annulus of a nickel iron alloy. The perforate vibrating member is bonded across the aperture of the support substrate, not directly bonded across the aperture of the piezoelectrical annulus. Use of such an apertured support substrate is typical of prior art atomiser or aerosol generators assemblies which require multi manufacturing steps to attach the piezo to the support substrate and seal the arrangement to render it impermeable to liquids. As discussed above, this type of arrangement risks dampening of the piezo actuation, corrosion of the metal substrate and short circuiting from moisture ingress between the piezo and substrate join areas. FIG. 4 shows a plan view of the unit where two metallisation electrodes can be found, the first being a drive electrode and the second an optional sense electrode. The specification discloses that these electrodes are electrically insulation through a 0.5 mm air gap between the electrode regions. The electrodes operate together to maintain resonant vibration of the actuator.

United States Publication No. US 2008/0308096 describes an aerosol generating device which includes a membrane for atomizing a liquid; an actuating device comprising a flexible substrate plate onto which a piezo actuating device is mounted. A membrane for aerosol generation is mounted onto the piezo actuating device within an aperture provided therein. The preferred flexible substrate plate material is described as flexible printed circuit boards or conductor boards onto which electrical conductors made of Cu, Ag, Al etc. are applied or boards in which such conductors are already integrated. The electrical conductors supply power to the piezo actuating device. It also describes how the actuating device is bonded or soldered onto the membrane and flexible substrate. In a number of the drawings indicate that the membrane has collar of variable width so that the actuating device can be completed or partially covered by the collar. In a preferred embodiment, it is taught to bond the membrane and the actuating device to a metal substrate which ensures occurrence of flexural oscillations.

International Publication No. WO 00/33972 describes an electrically switchable spray generator for simultaneously generating multiple streams of droplets. The device comprises a flexural plate onto which a plurality of actuator means are bonded such that the confluence of waves generated by vibration induced in the plate coincides with a linear array of nozzles. In one embodiment, the actuator means are said to be electroded by screen printed silver to within 0.5 mm of the top and bottom edges of the piezoelectric to enable electrical connection.

United States Publication No. US 2006/0207591 describes an aerosol generating assembly for inhalation therapy devices, in which an oscillatable assembly, consisting of a membrane, a piezo electric oscillation generator and a substrate to which the membrane is attached, is mounted in an encapsulating means such that at least the membrane is exposed for the supply of liquid and the generation of an aerosol, whereas the remaining parts of the oscillatable assembly are protected. Mounting occurs by means of a flexible passage which touches the assembly in the region of an oscillation nodal line, such that the oscillatory motions of the oscillatable assembly are not negatively affected. However, it is likely that the flexible nature of the passage may lead to problems arising from moisture ingress on vibration.

SUMMARY OF THE INVENTION

According to the present invention, there is provided an aerosol generator assembly comprising:

a vibratable body having first and second opposing sides, an aperture defined in the vibratable body and extending through the body from the first side to the second side, the vibratable body being vibratable by application of an electrical signal thereto;

a vibratable member with pores defined therein, the vibratable member mounted across the aperture;

a layer of electrical contact material on at least one side of the vibratable body; and characterised in that, a contact material free-zone is provided on said at least one side about the aperture, and the contact material free-zone and said vibratable member being dimensioned so that the vibratable member is mountable to the vibratable body within the contact material free-zone.

Advantageously, the structural arrangement of the aerosol generator assembly of the invention is less prone to defects from corrosion and less prone to dampening of the actuation of the piezo ceramic actuator, since a substrate support is not required. Furthermore, the contact material free-zone decrease the risk of moisture induced shorting as described below and forms a convenient area for assembling the actuator into an inhalation device (described below). The invention is also set out in the appended claims.

The layer of electrical contact material comprises a film of conductive material coated onto the surface of the vibratable piezo ceramic body. The electrical contact free zone is provided on the vibratable piezo ceramic body about the aperture therein to provide, on the same side of the body, a surface region which is coated with the film of conductive material and a surface region which is not coated with the film of conductive material and onto which the vibratable member may be mounted.

The vibratable member engages the vibratable piezo ceramic body on top of the electrical contact material free-zone (within the electrical contact free zone) provide about the aperture therein, thereby cover the aperture on one side of the body.

Preferably the preferred aerosol generator assembly of the invention comprises:

a vibratable piezo ceramic body having first and second opposing sides, an aperture defined in the vibratable body and extending through the body from the first side to the second side and having a layer of electrical contact material on each side of the vibratable body, the vibratable body being vibratable by application of an electrical signal thereto;

a vibratable member with pores defined therein, the vibratable member mounted across the aperture; and an electrical contact material free-zone is provided on at least one side of the body about the aperture, characterised in that the electrical contact material free-zone and the vibratable member are dimensioned so that the vibratable member is mountable directly onto the vibratable body on top thereof within the electrical contact material free-zone such that a gap area free of electrode contact material is formed between the terminating edge of the electrical contact material and the periphery of the vibratable member.

Preferably, the vibratable member comprises a rimmed edge which is mounted onto the vibratable body within the electrical contact material free-zone to form the gap area.

The arrangement means that the vibratable member does not extend out of the contact material free-zone. The contact material free-zone is typically of width 1 to 3 mm of exposed ceramic material from the edge of the aperture. When mounted, the vibratable member and the contact material are laterally spaced apart. In other words, the arrangement is such that there is a space or a gap or border between the terminating edge of the contact material and a periphery (for example a rim edge) of the vibratable member. In other words, the gap area is formed about the aperture defined in the vibratable body at the edge of the aperture and about its perimeter. The gap area is completely free of contact material such that the (naked) piezo ceramic material is exposed in this area. Indeed, it is desirable that the vibratable member does not occupy the entire contact material free-zone and that there remains a border of the contact material free-zone about the vibratable member that the vibratable member does not occupy. This border area is typically of width 1 to 2 mm of exposed ceramic material. The gap or border area is important as, when the vibratable member is positioned over the aperture and its edges rest on the vibratable piezo ceramic body within the electrode free zone, it electrically insulates the terminating edge of the electrode contact material from the vibratable member. This has the effect that in the event of moisture or vapour ingress, the likelihood of electrical shorting is reduced as fluid such as moisture or vapour is less likely to contact the terminating edge of the electrode contact material as it has further to travel, that is across the gap or border area formed before reaching the electrically contact material. This gap or border area surrounding the vibratable member therefore greatly lessens the likelihood of electrical short-circuiting via moisture ingress along the vibratable body. The gap or border area can then be easily sealed or insulated requiring only a small amount of sealant compared to many prior art devices.

If the vibratable member has a rimmed edge or flanged portion, the vibratable member may be mounted onto the vibratable body electrode free-zone at this edge or flange. However, it is important that the vibratable member and the contact material are never in any superimposed arrangement, where one overlies the other. Instead, it is preferred that vibratable member only overlies the vibratable body in the contact material free-zone, as the gap or border area free of the film of electrode contact material is necessary to reduce circuit shorting.

Desirably, a sealing material occupies said border thus further preventing liquid from transferring from the vibratable member to the contact material. Suitably, such sealing takes place during incorporation of the assembly into an inhalation device. The combination of gap and gap sealing means there is a much reduced risk of shorting due to liquid reaching the contact material/piezo. As explained above, one of the major issues with prior art devices is that over time moisture ingress of liquid material (and/or atomised material) from the vibratable membrane can make its way into contact with the electrical contact material over time and causes a short circuit across the vibratable body ending the useful life of the device. This happens frequently in prior art devices despite attempts to create a sufficiently good seal to prevent fluid ingress.

The arrangement of the present invention is of great importance as it allows a hermetic seal to be formed on the vibratable body about the vibratable member and within the contact material free-zone, such that there is a seal disposed about the vibratable body within the gap formed between the electrical contact material and the vibratable member. This means that if there is aerosol fluid or vapour ingress along the vibratable member, the fluid will be prevented from coming into the direct contact with the electrical contact material required for shorting to occur.

The aerosol generator assembly of the invention is thus much less likely to fail due to creation of a short circuit between regions of the electrical contact material on opposing sides of the piezo ceramic body. A complete short circuit will occur when moisture bridges between the electrical contact material layers, for example on opposing sides of the vibratable body. Device failure due to such shorting can occur in prior art devices after a relatively brief period of use, disabling the device. The assembly of the invention is advantageous since with the electrical contact free zone and gap provided therein, the vibratable membrane does not sit directly over the electrical contact material. Any aerosol that may ingress does not create a short circuit path which would otherwise be completed from the top electrode through the vibratable membrane through aerosol produced and onto the bottom electrode to short circuit the device.

Furthermore, the sealing arrangement of the present invention is advantageous over existing polymer sealing methods as fewer production steps are required (no metal substrate is required), significantly less sealant materials are required and therefore production costs are reduced.

Desirably, the vibratable body is constructed from a piezo ceramic-based material to form an actuatable piezo ceramic body. Desirably, the vibratable body is annular or substantially disc shaped. Suitably, the piezo ceramic-based material is one with piezo electrical properties. Preferably, the vibratable body is made of a piezo electric material such as lead zirconate titanite (PZT) or the like. Preferably, a layer of electrical contact material, in form of a film of conducting material is provided on each of the opposing sides/faces of the vibratable body, typically by a screen printing, metalization or a sputter coating technique.

The vibratable member is adapted to repetitively move up and down in the vertical direction upon vibration imparted to it by the vibratable body. This oscillation motion causes a micropumping action so as to atomise a fluid by drawing fluid into the pores and ejecting it in an atomised state. Since the need for a substrate and large amounts of sealant materials are eliminated, dampening problems are avoided.

Typically, the vibratable member may take the form of an annular thin sheet of any suitable material whose properties provide a corrosive resistant, robust, yet flexible structure, for example, a metal or metal alloy or a suitable polymeric material. Desirably, the sheet has a thickness of between 10 and 100 microns, but more preferably between 30 and 60 microns. In the assembly, the vibratable member is desirably bonded into place on the vibratable body within the electrode free zone, on top of naked piezo ceramic material about the aperture provided therein. Desirably, the vibratable member is non planar in shape to assist in aerosol formation. Preferably, the vibratable member is curved for example dome-shaped to ensure improved aerosol formation. Suitably, the dome and aperture in the vibratable body are dimensioned so that, when mounted, the dome portion of the vibratable member may sit within the aperture occupying the area formed therein.

Advantageously, the apertures in the vibratable member may be tapered and reducing in cross-sectional area from a first side which is in contact with liquid to be atomised to a second side which ejects the atomised liquid. This aperture geometry is typical of current electroformed nozzle plate manufacturing process. Funnel shaped pores assist in aerosol particle formation.

The vibratable member may be mounted onto the vibratable body by a retaining collar or flange area, which allows the member to flex while providing a mounting means to mount the vibratable member to the vibratable body. Accordingly, the annular disc may be provided with rimmed edge surrounding the dome. This is useful for providing an area so that the disc may be mounted on top of the vibratable body such that the dome shape is centred upon and desirably within the aperture of the vibratable body.

The film of electrical contact material is for applying an electrical signal across the vibratable body in order to induce oscillation/vibration within it.

Generally, the layer or film of electrical contact material is coated on the vibratable body when the body is manufactured. In particular, in the present invention there is a layer of electrical contact material provided on both sides of the vibratable body and desirably a contact material free-zone is provided on at least one of said first and second sides about the aperture. Suitably, the contact material free-zone is provided on both sides of the body. This means an appropriate seal can be provided on opposing sides of the vibratable body, if required.

In one arrangement, the assembly of the invention further comprises a complimentary delivery cup and/or an ejection cup for enhancing the seal and operability of the assembly as described below.

Thus in a related aspect, there is provided a delivery cup, for example a medication cup, having a mouth that is dimensioned to mate with the vibratable piezo ceramic body about the aperture and mounted on the vibratable piezo ceramic body by attaching the mouth thereof to the vibratable body, the delivery cup forming a reservoir for liquid to be aerosolized by the vibratable member characterised in that the vibratable body comprises a gap or a border of the electrical contact material free-zone about the vibratable member that the vibratable member does not occupy and onto which the mouth of the delivery cup is mounted.

In a related aspect of the invention there is provided an aerosol generator assembly comprising:

a vibratable body having first and second opposing sides, an aperture defined in the vibratable body and extending through the body from the first side to the second side the vibratable body being vibratable by application of an electrical signal thereto;

a vibratable member with pores defined therein, the vibratable member mounted across the aperture; and a delivery cup, for example a medication cup, having a mouth that is dimensioned to mate with the vibratable body about the aperture and mounted on the vibratable body by attaching the mouth thereof to the vibratable body, the delivery cup forming a reservoir for liquid to be atomised by the vibratable member.

Suitably, the vibratable body is a vibratable piezo ceramic body.

Preferably, an electrical contact material free-zone is provided on at least one side of the body about the aperture.

Suitably, the electrical contact material free zone and the vibratable member are dimensioned so that the vibratable member is mountable directly onto the vibratable body on top of the electrical contact material free-zone such that a gap area free of electrode contact material is formed between the terminating edge of the electrical contact material and the periphery of the vibratable member.

The mouth of the delivery cup mates with the vibratable piezoceramic body about the aperture defined therein, and is mounted on the vibratable body by attaching the mouth thereof to the vibratable body within the electrode contact free, the delivery cup forming a reservoir for liquid to be atomised by the vibratable member.

The mouth of the delivery cup mates with the vibratable body over the electrode contact free zone, such that the gap or border around the aperture is seal or closed off by the mouth of the delivery cup. Sealant may be provided about the electrode contact free zone, the gap or border formed between the mounting edge of the vibratable member and the terminating edge of the film of electrical contact material, the mate or connection area. Thus the opportunity for fluid ingress for example moisture or vapour ingress is limited.

This provides a simple yet highly effective assembly that is easily sealed against liquid leakage, and which requires a minimum number of processing or manufacturing steps and does not require significant quantities of sealant materials to ensure a hermetic seal about the whole of the vibratable body. Undesired vibration dampening is also avoided through obviation of the need for support substrate, and significant quantities of sealant. Since the mate portion is about the central aperture of the vibratable body, rather than outer edges, vibrations or oscillation dampening is further reduced.

Desirably, the delivery cup is mounted on the vibratable body with a seal provided between the lower mouth of the delivery cup and the vibratable body. For example, a bonding material used to bond the delivery cup to the vibratable body forms an appropriate seal, as well as an electrical insulator. Note the vibratable member is sandwiched between the mouth of the delivery cup and the vibratable body (piezo). This again is an important arrangement as no liquid can pass outside of the boundary of the mouth of the delivery cup. Optionally, the delivery cup has a (decreasing) tapered profile towards its lower mouth. A second end (or upper mouth) of the delivery cup may be provided with a closure for retaining liquid to be aerosolized within the delivery cup. The delivery cup can thus act as a funnel for delivery of liquid to the vibratable member. As with the first aspect of the invention, it is desirable that a layer of electrical contact material is provided on the vibratable body; however, an electrical contact free zone is provided about the aperture. In one arrangement, the aperture has a circular shape and the electrical contact free zone is provided as an annular zone about the aperture. Desirably, in such an arrangement the mouth of the delivery cup is dimensioned to mate with the vibratable body about the aperture and within the electrical contact free zone. In such an arrangement, suitably, the mouth of the delivery cup is dimensioned so that it is smaller than the dimensions of the electrical contact free zone. This means that mating of the delivery cup to the vibratable body leaves a gap (border) between the contact material and the delivery cup. That gap or border may be provided with a seal for example formed by a sealant material. The arrangement advantageously isolates the moisture area associated with from the contact areas, thus reducing opportunity for moisture ingress from the region about the flexible nozzle plate membrane and associated piezo short-circuiting.

Preferably, the delivery cup is calibrated or graduated so that quantities of liquid therein may be easily determined.

In one embodiment, the delivery cup may be adapted or connected to a liquid supply source to assist in continuous generation of aerosolised material.

In a related aspect, the aerosol generating assembly of the invention is also provided with an ejection cup, having a mouth that is dimensioned to mate with the vibratable piezo ceramic body about the aperture and mounted on the vibratable piezo ceramic body by attaching the mouth thereof to the vibratable body, the ejection cup forming an ejection guide for ejected liquid aerosolized by the vibratable member.

The present invention further provides an aerosol generator assembly comprising:

a vibratable body having first and second opposing sides, an aperture defined in the vibratable body and extending through the body from the first side to the second side the vibratable body being vibratable by application of an electrical signal thereto;

a vibratable member with pores defined therein, the vibratable member mounted across the aperture; and an ejection cup, having a mouth that is dimensioned to mate with the vibratable body about the aperture and mounted on the vibratable body by attaching the mouth thereof to the vibratable body, the ejection cup forming an ejection guide for ejected liquid atomised by the vibratable member.

The mouth of the ejection cup mates with the vibratable body over the electrode contact free zone, such that the gap or border around the aperture is sealed or closed off by the mouth of the delivery cup. Sealant may be provided about the electrode contact free zone, the gap or border formed between the mounting edge of the vibratable member and the terminating edge of the film of electrical contact material, the mate or connection area.

Thus the opportunity for moisture or vapour ingress is limited.

This provides a simple yet highly effective assembly that is easily sealed against liquid leakage.

Desirably, the ejection cup is mounted on the vibratable body with a seal provided between the mouth of the ejection cup and the vibratable body. For example a bonding material used to bond the ejection cup to the vibratable body forms an appropriate seal. The vibratable member and vibratable body are sandwiched in position between the mouth of the delivery cup and the mouth of the ejection cup. The contact free zone about the mouth of the housing may be sealed with a moisture blocking sealant such as an epoxy.

In a preferred embodiment where a delivery cup also is provided, the delivery cup and the ejection cup will be on opposing sides of the vibratable body to form an atomiser assembly. The assembly defines a channel or a passageway in the central portion of the device in which fluid is provided to the rear of the vibratable member and provided as an aerosol on the other side of the vibratable member. Advantageously, the assembly ensures that the vibratable body and the electrical contact material provided thereon, is sealed from the central passageway portion of the device where fluid/liquid is atomised.

This again is an important arrangement as no liquid is outside the boundary (that is in the liquid/aerosol channel or passageway) of the mouth of the ejection cup. Optionally, the ejection cup has an (increasing) tapered profile away from its mouth. A second end of the ejection cup may be provided with a closure for when the device is not in use. The ejection cup can thus act as a discharge funnel for discharge of ejected atomised fluid. The ejection cup may be provided with a connector or mating adapter to allow the cup to be attached to a delivery means, for example, an inhalation mask or the like.

It is desirable to combine both the delivery cup and ejection cup aspects of the present invention to provide an aerosol generator assembly comprising:

a vibratable body having first and second opposing sides, an aperture defined in the vibratable body and extending through the body from the first side to the second side the vibratable body being vibratable by application of an electrical signal thereto;

a vibratable member with pores defined therein, the vibratable member mounted across the aperture;

a delivery cup, for example a medication cup, having a mouth that is dimensioned to mate with the vibratable body about the aperture and mounted on the vibratable body by attaching the mouth thereof to the vibratable body, the delivery cup forming a reservoir for liquid to be atomised by the vibratable member; and an ejection cup, having a mouth that is dimensioned to mate with the vibratable body about the aperture and mounted on the vibratable body by attaching the mouth thereof to the vibratable body, the ejection cup forming an ejection guide for ejected liquid atomised by the vibratable member.

As with all other aspects of the invention it is desirable that a layer of electrical contact material is provided on the vibratable body but that an electrical contact free zone (as described above) is provided about the aperture on at least one face (surface) of the vibratable body. In one arrangement, the aperture has a circular shape and the electrical contact free zone is an annular zone about the aperture on the upper face of the vibratable body in contact with the medication cup.

Desirably, in such an arrangement the mouth of the ejection cup is dimensioned to mate with the vibratable body about the aperture and within the electrical contact free zone (to overlie the electrical contact free zone, gap formed therein and the edge or flange of the mounted vibratable member). Alternatively, the mouth of the ejection cup is dimensioned so that it is smaller than the dimensions of the electrical contact free zone. This means that mating of the ejection cup to the vibratable body leaves a gap between the contact material and the ejection cup. That gap may be provided with a seal for example formed by a sealant material.

It is desirable to have both delivery and ejection cups for controlling the path of the fluid to be aerosolized and the path of the aerosolized fluid. In such an arrangement the vibratable body is the structural element to which both the delivery and ejection cups are attached.

The assembly defines a channel or a passageway in the central portion of the device in which fluid is provided to the rear of the vibratable member and provide as an aerosol on the other side of the vibratable member.

It is further desirable that the delivery cup and/or ejection cup are combined with the aspect of having an electrical contact material free-zone about the aperture on one or both sides of the vibratable body. This ensures that the vibratable body and the electrical contact material provided there on, is sealed from the central passageway portion of the device where fluid/liquid is aerosolized.

The vibratable body may be provided with electrical connectors, such as electrical leads for supply of a suitable electrical signal to the electrical contacts of the vibratable body. In one embodiment, the assembly may be adapted to facilitate connection to a power source. In one embodiment, the electrical connections may also be protected within such an arrangement.

A housing may be provided for housing the vibratable body and the vibratable member and, optionally further, one or both of the delivery cup and the ejection cup. In one embodiment, the ejection cup is integrally formed with a housing which also houses a delivery cup and the vibratable body and the vibratable member. Desirably, the housing further comprises a guide conduit through which electrical wires can be passed to provide an electrical signal to the vibratable body.

It will be appreciated that all aspects of the invention described herein may be combined in any desired arrangement. For example, optional and/or preferred features of one embodiment of the invention may be combined with optional and/or preferred features of another/other embodiment(s) of the invention.

BRIEF DESCRIPTION OF THE DRAWINGS

Additional features and advantages of the present invention are described in, and will be apparent from, the detailed description of the invention and from the drawings in which.

DETAILED DESCRIPTION OF THE INVENTION

It should be readily apparent to one of ordinary skill in the art that the examples disclosed herein below represent generalised examples only, and that other arrangements and methods capable of reproducing the invention are possible and are embraced by the present invention.

Figures 1A, 1B:
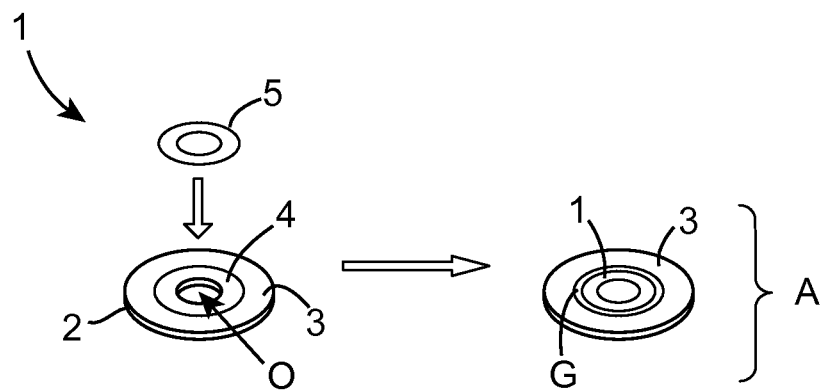
FIG. 1A illustrates a vibratable membrane component and a piezo ceramic ring component of a typical vibratable piezo ceramic body arrangement of the present invention.
FIG. 1B illustrate an assembled piezo ceramic in which the vibratable membrane is mounted onto the vibratable piezo ceramic body across the aperture of the piezo ceramic ring of FIG. 1A.

Referring now to the drawings and specifically FIGS. 1 to 5 inclusive and initially FIGS. 1A and 1B. FIG. 1A shows the individual components of a piezo ceramic actuator A according to the present invention, as illustrated generally by reference sign A. The piezo ceramic actuator A comprises a flexible nozzle/membrane plate 1 and an annular piezo ceramic body 2 (vibratable piezo ceramic body) having a centrally disposed aperture O disposed therein. The annular piezo ceramic body 2 is surface coated with a film of electrical contact material 3, except in the region about the centrally disposed aperture O which is not coated with electrical contact material 3. This forms an area of electrical contact free zone 4 (that is an area of the surface of the piezo ceramic body which is not coated with a film of electrical contact material) about the perimeter of aperture O and an area where the film of electrical contact material is present. The flexible nozzle/membrane plate 1 is dome shaped (as shown in FIGS. 3A & 3B) and comprises a retaining collar or flange 5 to facilitate mounting nozzle/membrane plate 1 onto the annular piezo ceramic body 2 such that the dome of the nozzle/membrane plate 1 resides within aperture O of the annular piezo ceramic body 2 (see down arrow of FIG. 1A) and such that the retaining collar or flange 5 sits on top of the vibratable body within the electrical contact free zone 4. The mouting arrangement is in such a manner that an insulating border or gap G of naked (exposed) piezo ceramic material is formed between the edge of the retaining collar 5 of the mounting nozzle/membrane plate 1 and the terminating edge of the film of the electrical contact material 3 present on the surface of the piezo ceramic vibratable body about the aperture provided therein (see FIG. 1B for the assembled piezo ceramic actuator A assembly). The border or gap G is therefore formed as an annular ring of the naked surface of the annular piezo ceramic body 2, which is not coated with the film of electrical contact material 3.

Figure 2:
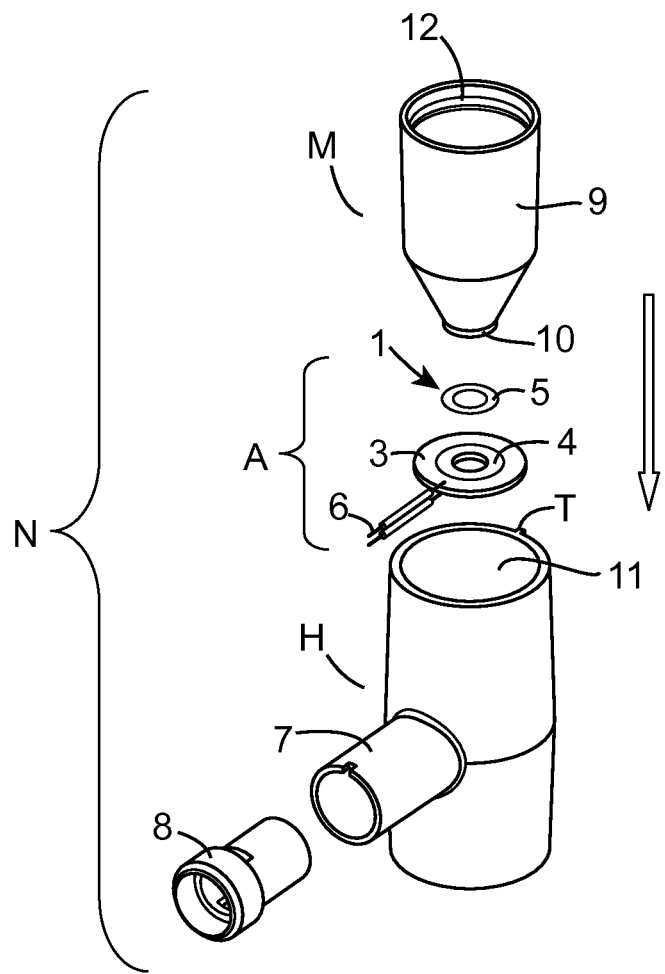
FIG. 2 shows an exploded view of the component parts of an aerosol generator of the present invention.

Turning now to FIG. 2, which illustrates the component parts of an aerosol generator assembly N of the present invention. The component parts of the aerosol generator assembly N of Figure IB are shown. The annular piezo ceramic body 2 (vibratable piezo ceramic body) of piezo ceramic actuator A is provided with a pair of electrical contact connectors 6 for supplying electricity to the film of electrical contact material coated onto the surface of the piezo ceramic body 2 (vibratable piezo ceramic body). The electrical contact connectors 6 contact a portion of the film of electrical contact material 3 on each of the opposite sides of the annular piezo ceramic body 2, thus completing a circuit and allowing current to pass through the piezo ceramic body to induce vibration. FIG. 2 shows aerosol generator housing H, which is assembled around piezo ceramic actuator A in the assembled device. The lower part of aerosol generator housing H is provided with a protecting sleeve 7 for accommodating and protecting electrical contact connectors 6. A plug adapter 8 is also shown and is adapted to be insertable into protecting sleeve 7. The plug adapter 8 mates with the terminals of electrical contact connectors 6 to form a plug type arrangement, which allows an electrical power cable (not shown) to be removeably plugged into the plug adapter 8, when the device is ready for use. The aerosol generator assembly N also comprises a medication cup M which serves as a reservoir and funnel for medication to be aerosolized. The medication cup M comprises walls 9 which taper inward towards the bottom of the cup to form a funnel shaped mouth. At the bottom of the cup M, the walls form a rim 10. The medication cup M is dimensioned to be snugly accommodated into the mouth 11 of the aerosol generator housing H to seal off the piezo ceramic actuator A from outside and to complete the aerosol generator assembly N. The medication cup M is provided with a further rim 12 about the head of the medication cup to facilitate addition of a cap 13 (shown in FIG. 3A and 3B). The aerosol generator housing H is provided with tabbed spine T which runs part way down the housing to assist inserting the device into an inhalation mask in the correct orientation.

Figure 3A:
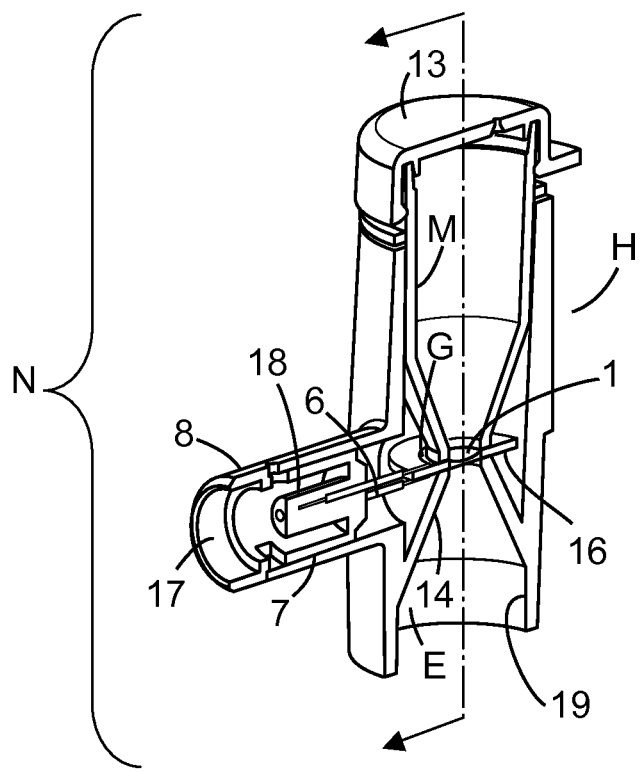
FIG. 3A shows a perspective view of line section through an assembled aerosol generator of the invention.
Figure 3B:
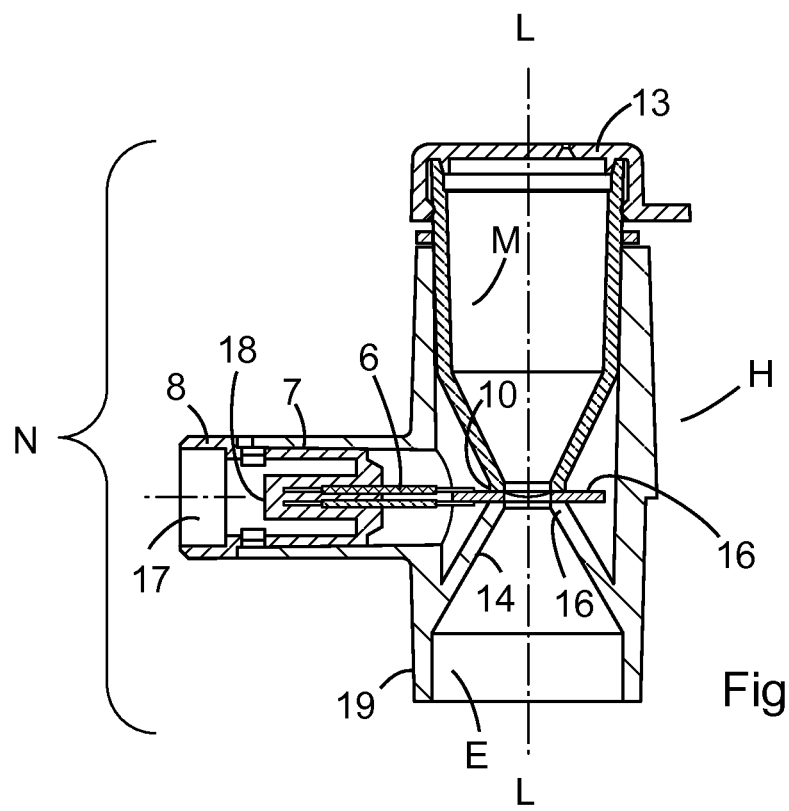
FIG. 3B shows a side view through section line L-L of FIG. 3A.

FIG. 3A shows a diagonal section through the assembled aerosol generator assembly N of the invention and FIG. 3B shows a section through line L-L as shown in FIG. 3A. The ejection cup E forms the lower part of the housing H. In this example, the ejection cup E is shaped as an inverted funnel to assist in delivering generated aerosol. In other words, walls 14 of ejection cup E taper inwards towards the top of the ejection cup E. The upper surface of the tapered ejection cup walls 14 form a flat rim 15 dimensioned such that the piezo ceramic actuator A sits on top of and is supported by the flat rim 15 of the ejection cup E. The walls 9 of the medication cup M tapered inwards towards the bottom of the medication cup M to form a rim 10 and are dimensioned to match that of the rim 15 of the ejection cup E. When the medication cup M is inserted into the housing H, rim 10 of the medication cup M rests over the piezo ceramic actuator A in exactly the opposite position to rim 15 of the ejection cup E. The cross section views clearly show the piezo ceramic actuator A sandwiched between inserted medication cup M and an ejection cup E in a supported or mounted position in such matter that the outer portion 16 of the annular piezo ceramic body 2 is suspended freely in an unobstructed manner. Furthermore, the sandwich arrangement is such that the rim 10 of the medication cup M sits within the electrical contact free area 4 on the upper surface of the annular piezo ceramic body 2 of the piezo ceramic actuator A, while maintaining electrical contact free gap or border G about the periphery of rim 10 of the medication cup M. FIG. 3A shows a particular clear view of the dome shaped nozzle/membrane plate 1 which is held in position between the rim 10 of the medication cup M and the upper surface of the annular piezo ceramic body 2 in the electrical contact free zone 4 leaving electrical contact free gap G about the periphery of rim 10 of the medication cup M. The electrical contact free gap G may then be sealed with moisture resistant material for example epoxy to bond the components together (not shown in the Figures). The arrangement means that the dome shaped nozzle/membrane plate 1 is completely hermetically sealed or isolated from the electrical contact material 3 of the upper surface of the annular piezo ceramic body 2. The epoxy further improves the seal and stabilises the piezo ceramic actuator A within the housing H. The entire arrangement protects the electrical contact area 3 from the effects of moisture ingress from the area where the nozzle/membrane plate 1 is mounted onto the annular piezo ceramic body 2. FIGS. 3A and 3B clearly show the protecting sleeve 7 which protects the electrical contact connectors 6. Plug adapter 8 has a central portion 18, which is adapted to house the terminating ends of the electrical contact connectors 6 to provide a power plug arrangement. The mouth 17 of the plug adapter 8 is adapted for connection to a power lead (not shown). The bottom portion of ejection cup E remote from the inwardly tapered walls 14 is straight to form a tube portion 19 which can be fitted to an inlet of a medication inhalation mask or the like (see for example, medication inhalation mask of European Patent Application No. 9170868.5). The cap 13 is also provided with a ringed tether portion T which sits about the neck of the housing and prevents loss of the cap 13 when it is not in the closed position.

Figure 4A:
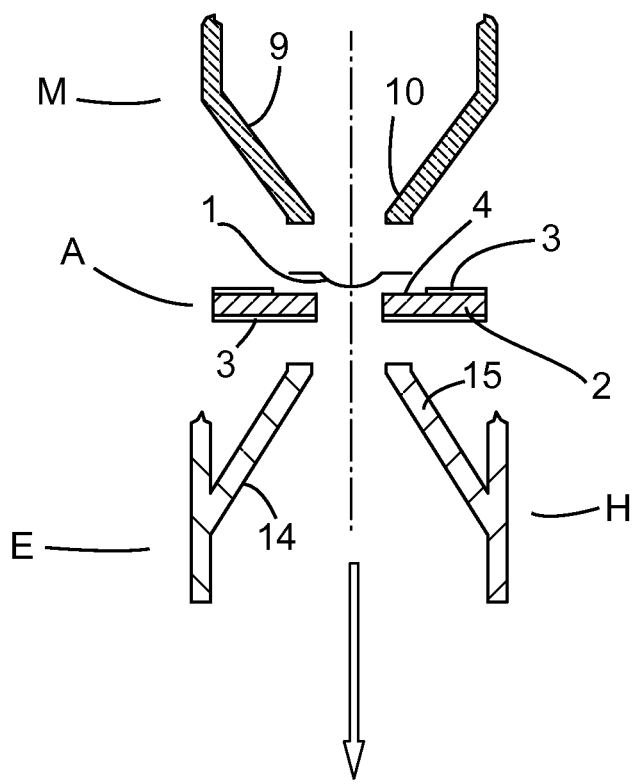
FIG. 4A shows an exploded view of the component parts of an aerosol generator of the present invention.
Figure 4B:
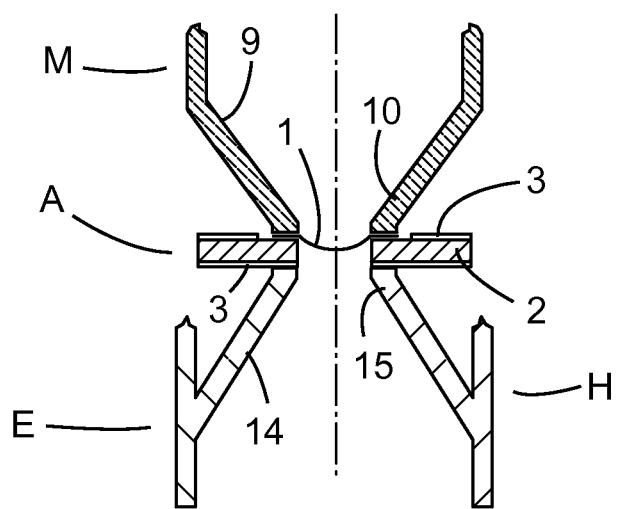
FIG. 4B shows the components parts of FIG. 4A in assembled state.

FIG. 4A shows a sketch of an exploded view of the piezo ceramic actuator A sandwiched between the medication cup M and the ejection cup E mounted within housing H of the aerosol generator assembly N of the present invention. FIG. 4B shows the components of FIG. 4A in the normal assembled position. FIGS. 4A and 4B clearly shows the opposing configurations of the tapered rim 10 of the medication cup M and tapered rim 15 of the ejection cup E. The dome shaped nozzle plate 1 is dimensioned to fit within aperture O of the annular piezo ceramic body 2. Retaining collar or flange 5 is dimensioned to overlie a portion of the electrical contact free zone 4 on the upper surface of annular piezo ceramic body 2. The electrical contact material 3 is clearly indicated by thick black line in the sketches. The funnel shape of the medication cup M is clearly shown in FIGS. 4A and 4B as is the inverted funnel shape of the ejection cup E which forms part of housing H. The drawings illustrate that when mounted within aperture O of the annular piezo ceramic body 2, retaining collar 5 of the nozzle/membrane plate 1 does not touch any area of the electrical contact material 3 the annular piezo ceramic body 2. In other word, the border or gap G of electrical contact free space 4 is maintained about the perimeter of the nozzle/membrane plate 1 and the area of electrical contact material 3.

Figure 5:
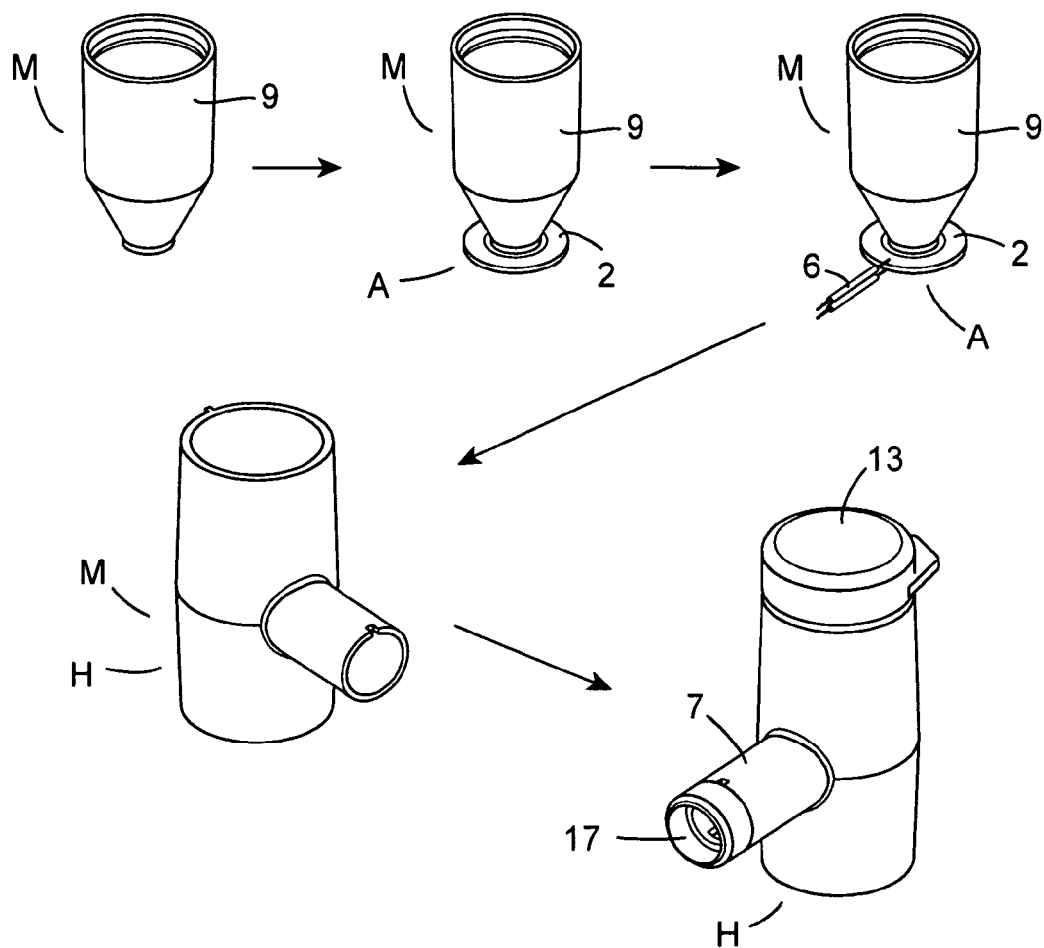
FIG. 5 shows assembly steps for manufacturing an aerosol generator assembly of the present invention.

FIG. 5 shows assembly steps for manufacturing an aerosol generator assembly of the present invention in which medication cup M is bonded to the piezo ceramic actuator A with dome shaped nozzle plate 1 sandwiched between the rim 10 of the medication cup M and the annular piezo ceramic body 2. Electrical connector leads 6 are then connected to the electrical contact material 3 on the upper and lower surfaces of the annular piezo ceramic body 2. The housing H is then assembled around the medication cup M/ piezo ceramic actuator A sub-assembly. Cap 13 can then be fitted to the device as required.

In use, a power cable is inserted into the mouth 17 of the plug adapter 8 to provide electrical power to the aerosol generator assembly N. Liquid medicament to be dispensed is placed into the medication cup M. The liquid fills the funnel shaped inner chamber of medication cup M and rests over the dome shaped nozzle/membrane plate 1. Cap 13 may then be placed over the upper mouth of medication cup M so that the liquid medicament does not spill out of the aerosol generator assembly N. Power is turned on and flows through the electrical contact material of the upper and lower surfaces of the annular piezo ceramic body 2 to produce oscillations in the annular piezo ceramic body 2 which are transferred to dome shaped nozzle/membrane plate 1, to induce a vertical flexing action in the membrane plate 1. The flexing motion forces fluid at the upper surface of the dome shaped nozzle/membrane plate 1 through funnel shaped apertures in the dome shaped nozzle/membrane plate 1 by way of a micropumping action. The liquid exits the apertures in dome shaped nozzle/membrane plate 1 as an aerosol. The shape of inverted funnel shaped ejection cup E allows the generated aerosol to flow more efficiently out of the device. Ingress of moisture along the dome shaped nozzle/membrane plate 1 does not reach electrically contact material electrical contact material 3 easily due to the electrical contact material gap G between the mounting area of dome shaped nozzle/membrane plate 1 to the annular piezo ceramic body 2 and sealant provided therein.

The words "comprises/comprising" and the words "having/including" when used herein with reference to the present invention are used to specify the presence of stated features, integers, steps or components but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The invention claimed is:

1. An aerosol generator assembly comprising:
   a vibratable piezo ceramic body having first and second opposing sides, an aperture defined in the vibratable piezo ceramic body and extending through the body from the first side to the second side and having a layer of electrical contact material on each side of the vibratable piezo ceramic body, the vibratable piezo ceramic body being vibratable by application of an electrical signal thereto;
   a vibratable member with pores defined therein, the vibratable member mounted across the aperture; and
   an electrical contact material free-zone is provided on at least one side of the vibratable piezo ceramic body about the aperture,
   wherein the electrical contact material free-zone and the vibratable member are dimensioned so that the vibratable member is mountable onto the vibratable piezo ceramic body on top thereof within the electrical contact material free-zone such that a gap area free of the layer of electrical contact material is formed between the terminating edge of the layers of electrical contact material and the periphery of the vibratable member, thus electrically insulating the terminating edge of the electrical contact material from the vibratable member.

2. The aerosol generator assembly of claim 1 wherein the layer of electrical contact material comprises a film of conductive material coated onto the surface of the vibratable piezo ceramic body.

3. The aerosol generator assembly of claim 2 wherein the electrical contact free zone is provided on the vibratable piezo ceramic body about the aperture therein to provide, on the same side of the vibratable piezo ceramic body, a surface region which is coated with the film of conductive material and a surface region which is not coated with the film of conductive material and onto which the vibratable member may be mounted.

4. The aerosol generator assembly of claim 1 wherein the vibratable member engages the vibratable piezo ceramic body on top of the electrical contact material free-zone provides about the aperture therein, thereby covering the aperture on one side of the vibratable piezo ceramic body.

5. The aerosol generator assembly of claim 1 wherein the vibratable member comprises a rimmed edge which is mounted onto the vibratable piezo ceramic body within the electrical contact material free-zone to form the gap area.

6. The aerosol generator assembly according to claim 1 further comprising a delivery cup having a mouth that is dimensioned to mate with the vibratable piezo ceramic body about the aperture and mounted on the vibratable piezoceramic body by attaching the mouth thereof to the vibratable piezo ceramic body, the delivery cup forming a reservoir for liquid to be aerosolized by the vibratable member.

7. The aerosol generator assembly to claim 6 wherein the mouth of the delivery cup is dimensioned to mate with the vibratable piezo ceramic body about the aperture and within the electrical contact free zone.

8. The aerosol generator assembly according to claim 6 wherein the delivery cup is mounted on the vibratable piezo ceramic body with a seal provided between the mouth of the delivery cup and the vibratable piezo ceramic body.

9. The aerosol generator assembly according to claim 6, wherein the delivery cup-is a medication cup.

10. The aerosol generator assembly according to claim 6, wherein the vibratable piezo ceramic body comprises a gap or a border of the electrical contact material free-zone about the vibratable member that the vibratable member does not occupy and onto which the mouth of the delivery cup is mounted.

11. The aerosol generator assemble according to claim 1 further comprising an ejection cup, having a mouth that is dimensioned to mate with the vibratable piezo ceramic body about the aperture and mounted on the vibratable piezo ceramic body by attaching the mouth thereof to the vibratable piezo ceramic body, the ejection cup forming an ejection guide for ejected liquid aerosolized by the vibratable member.

12. The aerosol generator assembly according to claim 1 wherein a sealing material is provided within the electrical contact free zone.

13. The aerosol generator assembly according to claim 1, further comprising electrical connectors for connecting the layer of electrical contact material on opposing faces of the vibratable piezo ceramic body for supply of a suitable electrical signal to the electrical contact material.

* * * * *